United States Patent [19]
Alburn et al.

[11] B  3,981,915
[45] Sept. 21, 1976

[54] AMIDES OF 1-AMINOCYCLOPENTANE CARBOXYLIC ACID

[75] Inventors: Harvey E. Alburn, West Chester; Norman H. Grant, Wynnewood, both of Pa.

[73] Assignee: American Home Products Corporation, New York, N.Y.

[22] Filed: Aug. 6, 1973

[21] Appl. No.: 386,257

[44] Published under the second Trial Voluntary Protest Program on February 3, 1976 as document No. B 386,257.

Related U.S. Application Data

[63] Continuation of Ser. No. 209,335, Dec. 17, 1971, Pat. No. 3,803,229.

[52] U.S. Cl. ............................. 260/557 R; 424/320
[51] Int. Cl.² ...................................... C07C 103/737
[58] Field of Search .................................... 260/557

[56] References Cited
UNITED STATES PATENTS
3,803,229  4/1974  Alburn et al. ........................ 260/557

*Primary Examiner*—Harry I. Moatz
*Attorney, Agent, or Firm*—Stephen Venetianer

[57] ABSTRACT

The compounds are amides of 1-aminocyclopentanecarboxylic acid, having valuable pharmacodynamic properties in that they are active against Columbia SK polio virus in warm-blooded animals.

1 Claim, No Drawings

AMIDES OF 1-AMINOCYCLOPENTANE CARBOXYLIC ACID

This application is a continuation of application Ser. No. 209,335 filed Dec. 17, 1971, now U.S. Pat. No. 3,803,229, granted Apr. 9, 1974.

DESCRIPTION OF THE INVENTION

This invention relates generally to novel chemical compounds having valuable pharmacodynamic properties and to processes for preparing said compounds. The novel compounds of the invention are the amides of 1-aminocyclopentanecarboxylic acid encompassed within the following general formula:

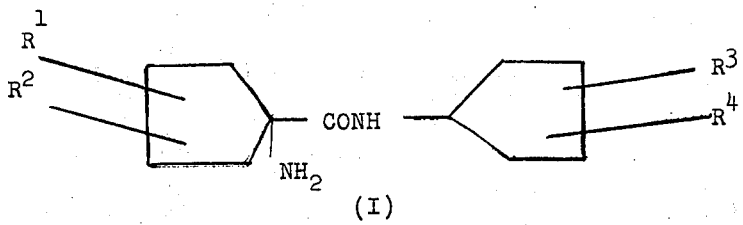

wherein $R^1$, $R^2$, $R^3$ and $R^4$ are each selected from the group consisting of hydrogen, lower alkyl, lower alkoxy, hydroxy, halogen, and nitro; and the pharmaceutically-acceptable acid-addition salts thereof.

The novel compounds of formula (I) may conveniently be prepared by heat-reacting a selected N-carboxyanhydride of 1-aminocyclopentanecarboxylic acid with a cyclopentylamine in accordance with the following reaction scheme:

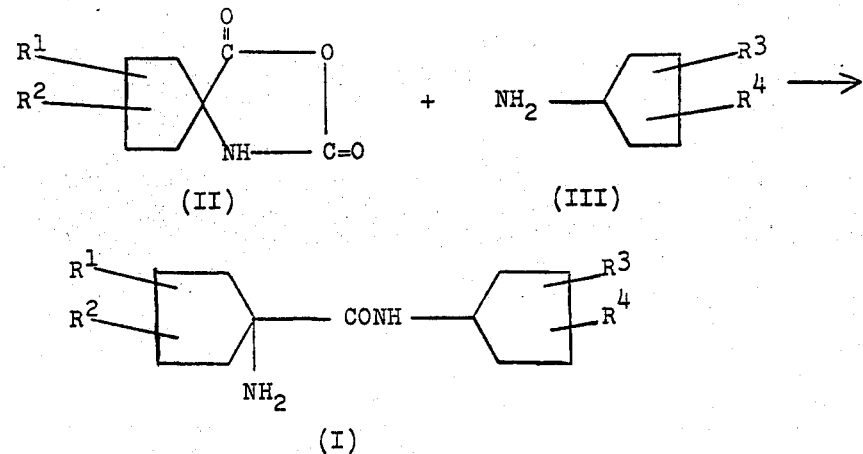

wherein $R^1$, $R^2$, $R^3$ and $R^4$ have the same meaning described hereinbefore.

The reactants (III), the suitable derivatives of cyclopentylamine, employed in the preparative process illustrated by the above reaction scheme may readily be prepared by known synthesis for adding the desired substituents in the ring of cyclopentylamine per se. The reactants (II), the N-carboxyanhydrides of 1-aminocyclopentanecarboxylic acid, which are not commercially available, can easily be prepared in accordance with standard organic procedures will known to those skilled in the art. For example, a procedure which has been employed to synthesize the anhydrides of formula (II) above utilized in the preparation of compound (I) of the present invention, is described in U.S. Pat. No. 3,206,455, "Process for Producing 6-(α-aminoacylamino) Penicillanic Acids", H. E. Alburn and N. H. Grant.

It has been discovered that compounds of formula (I) meeting the described qualifications have valuable pharmacological properties. More specifically, said compounds have been found to have unexpected activity against Columbia SK polio virus, as referred to in greater detail hereinafter.

In the pharmacological evaluation of the properties of the compounds of this invention, the effects in vivo of the compounds are tested by the following procedure against Columbia SK polio virus:

The hosts may be any standard experimental animals, such as mice, ferrets and rabbits, and the like, but mice are the preferred test subjects, and the test procedures described here are in regard to the use of mice weighing from 14 to 15 grams as hosts.

Prior to use of the selected seed virus pools in the tests, all are titrated for infectivity, and the challenge dose used is one which will kill almost all of the non-treated control animals ($LD_{100}$).

Columbia SK polio is inoculated intra-peritoneally. The soluble compounds to be tested are dissolved in an isotonic solution, while the insoluble compounds to be tested are ground, then suspended in 0.5 percent carboxymethylcellulose (CMC) or the like.

The test compounds are then administered at various dose levels depending upon the activity of the compound, each dose level being subcutaneously administered to each of a group of ten mice. Two control groups of ten mice each are not treated with the test compounds. Treatment may be started as early as 24 hours before infection or delayed until after infection, and the best dosage schedule used is determined for each compound. The observation period for mice infected with polio virus is 14 days.

The parameters used for evaluating the effectiveness of the test compounds are percentage of survivors, geometric mean survival time, and the Rank T test. When there are survivors among the control animals, a Rank T test is employed. The Rank T test compares the pattern of deaths among the treated animals with the pattern of deaths among the control animals and is a measure of the prolongation of life produced by the compound being tested. The geometric mean survival time is determined by computation when there are no survivors among the control animals.

The scores for the treated animals are compared statistically with the scores of the control group. The accepted standard of $P<0.05$ is required for significance. In this regard, a mode of challenging the animals with the compounds of Formula (I) with respect to amounts thereof administered and time schedule of such post infection treatment, and a mode of compiling the results of the challenge are illustrated in Tables I. and II., respectively, of U.S. Pat. No. 3,555,044.

It has been found that the physical form of the test compound is important. Best results are obtained by micronization, that is, by grinding the test compound to a maximum particle size of less than five microns ($<5\mu$).

An effective dose range against Columbia SK polio virus has been found to be 4 to 10 mg. in mice weighing 14 to 15 grams.

When the compounds of this invention are employed as described above, they may be administered alone or in combination with pharmaceutically acceptable carriers, the proportion of which is determined by the solubility and chemical nature of the compound, chosen route of administration and standard pharmaceutical practice. For example, they may be administered orally in the form of tablets or capsules containing conventional excipients such as starch, milk, sugar, certain types of clay and so forth. They may be administered orally in the form of suspensions or solutions, or they may be injected parenterally, that is intramuscularly, intravenously or subcutaneously. For parenteral administration they may be used in the form of a sterile solution containing other solutes, for example, enough saline or glucose to make the solution isotonic.

The dosage of the present therapeutic agents will vary with the form of administration and the particular compound chosen. Furthermore, it will vary with the particular animal under treatment. It will generally be found that, when the composition is administered orally, larger quantities of the active agent will be required to produce the same effect as a smaller quantity given parenterally. In general, the compounds of this invention are most desirably administered at a concentration level that will generally afford effective results without causing any harmful or deleterious side effects.

The terms and expressions which have been employed are used as terms of description and not of limitation, and there is no intention in the use of such terms and expressions of excluding any equivalents of the features shown and described or portions thereof, but it is recognized that various modifications are possible within the scope of the present invention which is illustrated by the following Examples:

EXAMPLE I

1-Amino-N-cyclopentylcyclopentanecarboxamide

A mixture of 1.1 g of cyclopentylamine, 2 g of N-carboxy-1-aminocyclopentanecarboxylic acid anhydride and 25 ml. of dioxane was thoroughly mixed and then allowed to stand at room temperature for 18 hours. The system was filtered, and the filtrate was evaporated to an oil. The oil was dissolved in 20 ml. of ethanol containing 20 meq of HCl and then evaporated to dryness. The product was soluble in acetone, water, ethanol, dimethylacetamide, and dimethylformamide but not in ethyl acetate or dioxane. It was recrystallized from acetone.

Calculated for $C_{11}H_{20}ON_2 . HCl. ½ H_2O$: C, 54.8; H, 9.2; Cl, 14.8; Found: C, 54.6; H, 9.1; Cl, 14.0.

The product is active against influenza virus HNS and Columbie SK polio virus as indicated by the test described hereinbefore.

EXAMPLE II

Following the procedure of Example I, each of a series of N-carboxyanhydrides of 1-aminocyclopentanecarboxylic acid derivatives is respectively reacted with a selected cyclopentylamine derivative to prepare the amides of 1-aminocyclopentanecarboxylic acid of Formula I, each having the antiviral activity referred to hereinbefore. The reactants, and final products of Formula I of the invention resulting therefrom, are given in the Table below:

TABLE

| NCA of 1-Aminocyclopentane-carboxylic Acid | Cyclopentylamine Derivative | Amide of 1-Amino-cyclopentane-carboxylic Acid |
|---|---|---|
| N-carboxy-2-methyl-1-amino-cyclopentanecarboxylic acid | 4-chloro-cyclopentylamine | 1-amino-2-methyl-N-(4-chlorocyclopentyl)cyclopentanecarboxamide |
| N-carboxy-2-ethoxy-3-propyl-1-amino-cyclopentanecarboxylic acid | 5,6-dimethyl-cyclopentylamine | 1-amino-2-ethoxy-3-propyl-N-(5,6-dimethyl-cyclopentyl)cyclopentanecarboxamide |
| N-carboxy-2-ethoxy-1-aminocyclopentanecarboxylic acid | 7-methoxy-cyclopentylamine | 1-amino-2-ethoxy-N-(7-methylcyclopentyl)cyclopentanecarboxamide |
| N-carboxy-3-hydroxy-1-amino-cyclopentanecarboxylic acid | 6-nitro-cyclopentylamine | 1-amino-3-hydroxy-N-(6-nitrocyclopentyl)cyclopentanecarboxamide |
| N-carboxy-2-bromo-1-aminocyclopentanecarboxylic acid | 5-amino-cyclopentylamine | 1-amino-2-bromo-N-(5-aminocyclopentyl)cyclopentanecarboxamide |
| N-carboxy-3-nitro-1-aminocyclopentaneboxylic acid | 4-hydroxy-cyclopentylamine | 1-amino-3-nitro-N-(4-hydroxycyclopentyl)cyclopentanecarboxamide |
| N-carboxy-2-methyl-3-fluoro-1-amino-cyclopentanecarboxylic acid | 4-propyl-6-amino-cyclopentylamine | 1-amino-2-methyl-3-fluoro-N-(4-propyl-6-amino-cyclopentyl)-cyclopentanecarboxamide |

We claim:

1. An amide of 1-aminocyclopentanecarboxylic acid of the compound having the following formula:

wherein $R^1$ is selected from the group consisting of hydrogen, lower alkoxy, hydroxy, lower alkyl and nitro; $R^3$ is selected from the group consisting of hydrogen, lower alkyl, halogen and hydroxy and $R^4$ is either lower alkyl or hydrogen with the proviso that $R^3$ is either hydroxy or hydrogen when $R^4$ is lower alkyl; with the further proviso that $R^1$, $R^3$ and $R^4$ are not all hydrogen.

* * * * *

UNITED STATES PATENT OFFICE
CERTIFICATE OF CORRECTION

Patent No. 3,981,915    Dated September 21, 1976

Inventor(s) Harvey E. Alburn et al.

It is certified that error appears in the above-identified patent and that said Letters Patent are hereby corrected as shown below:

The term of this patent subsequent to April 9, 1991 has been disclaimed.

Signed and Sealed this

Twelfth Day of October 1976

[SEAL]

Attest:

RUTH C. MASON
Attesting Officer

C. MARSHALL DANN
Commissioner of Patents and Trademarks